United States Patent [19]

Nisato et al.

[11] Patent Number: 4,526,995

[45] Date of Patent: Jul. 2, 1985

[54] 3-AMINO-N-[2-(5-DIMETHYLAMINOME-THYLFURAN-2-YLMETHYLTHIO)ETHYL]-BENZAMIDE INTERMEDIATE

[75] Inventors: Dino Nisato, Pavia; Sergio Boveri, Tortona, both of Italy

[73] Assignee: Sanofi, Paris, France

[21] Appl. No.: 634,569

[22] Filed: Jul. 26, 1984

Related U.S. Application Data

[62] Division of Ser. No. 511,107, Jul. 6, 1983, Pat. No. 4,492,711.

[30] Foreign Application Priority Data

Aug. 13, 1982 [FR] France .................. 82 14125

[51] Int. Cl.³ .......................... C07D 307/54
[52] U.S. Cl. .................... 549/494
[58] Field of Search ....................... 549/494

[56] References Cited

U.S. PATENT DOCUMENTS 4,318,858  3/1982  Hirai et al. .................. 549/494

4,439,444  3/1984  Nisato et al. .................. 549/494 X

Primary Examiner—Richard L. Raymond
Attorney, Agent, or Firm—Stevens, Davis, Miller & Mosher

[57] ABSTRACT

Benzamides having histamine $H_2$ receptor blocking activity of formula

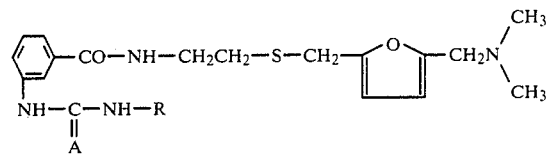

wherein A represents O, S, N—CN or CH—$NO_2$ and R represents an alkyl group or an optionally substituted phenyl, pyridyl or pyridyl 1-oxide group; their salts; a process for their preparation; and pharmaceutical compositions containing them as active ingredients.

1 Claim, No Drawings

3-AMINO-N-[2-(5-DIMETHYLAMINOMETHYLFURAN-2-YLMETHYLTHIO)ETHYL]BENZAMIDE INTERMEDIATE

This is a division of application Ser. No. 511,107 filed July 6, 1983, now U.S. Pat. No. 4,492,711.

The present invention relates to ureido, thioureido, cyanoguanidino and nitroethenediamino benzamides having a histamine $H_2$ receptor blocking activity, to their salts, to a process for their preparation and to pharmaceutical compositions containing them as active ingredients.

The French published patent application No. 2 471 376 describes and claims compounds of formula

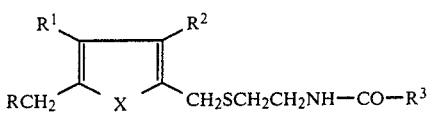

wherein R is the dimethylamino or 1-pyrrolidinyl group; $R^1$ and $R^2$ are each hydrogen or an alkyl group of from 1 to 3 carbon atoms; $R^3$ is hydrogen, an alkyl group of from 1 to 3 carbon atoms (optionally substituted by a member selected from the group consisting of cyano, alkoxy of from 1 to 3 carbon atoms, phenyl and pentagonal or hexagonal heterocyclic groups), a cycloalkyl group of from 3 to 6 carbon atoms, an alkenyl group of from 2 to 5 carbon atoms (optionally substituted by a member selected from the group consisting of alkoxy of from 1 to 3 carbon atoms, phenyl and phenoxy groups), an aryl group of from 6 to 10 carbon atoms (optionally substituted by one or two members selected from the group consisting of hydroxy, halogen, nitro, sulfamoyl, alkyl of from 1 to 3 carbon atoms, alkoxy of from 1 to 3 carbon atoms, alkanoyl of from 1 to 3 carbon atoms, alkoxycarbonyl of from 2 to 4 carbon atoms, dialkylamino of from 2 to 4 carbon atoms and alkanesulfonyl of from 1 to 3 carbon atoms), or a pentagonal or hexagonal heterocyclic group (optionally substituted by a member selected from the group consisting of oxo, halogen, alkyl of from 1 to 3 carbon atoms and alkoxy of from 1 to 3 carbon atoms) and X is oxygen or sulfur, as well as their pharmaceutically acceptable acid addition salts.

Among the compounds described in the above-mentioned patent, the compound of formula I where R=dimethylamino, $R^1=R^2=H$, and $R^3=$4-sulfamoylphenyl, namely the N-[2-(5-dimethylaminomethylfuran-2-ylmethylthio)ethyl]-4-sulfamoylbenzamide, as oxalate, shows an ED50 of 2.54 mg/kg in the gastric acid secretion inhibiting activity in the rat.

The above-mentioned French patent application in its general formula does not include any benzamide substituted in the benzene ring by an ureido, thioureido, guanidino or nitroethenediamino group.

It has now been found that novel benzamides having an ureido, thioureido, guanidino or nitroethenediamino group in the meta position of the benzamide phenyl ring possess a good action antagonizing the histamine $H_2$ receptors.

Thus, according to one of its embodiments, it is an object of the present invention to provide benzamides of formula

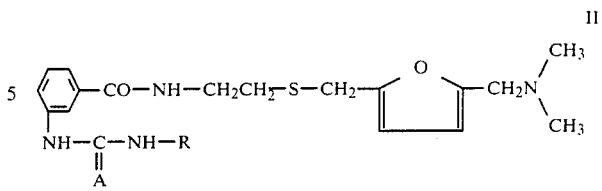

wherein A represents a oxygen or sulfur atom or a N—CN or CH—$NO_2$ group and P represents an alkyl group of from 1 to 6 carbon atoms, or an optionally substituted phenyl, pyridyl or pyridyl-1-oxide group as well as their pharmaceutically acceptable salts.

The pharmaceutically acceptable salts include the nontoxic salts derived from mineral or organic acids such as hydrochloride, hydrobromide, sulfate, succinate, tartrate, citrate, fumarate, maleate, 4,4'-methylene-bis-(3-hydroxy-2-naphtoate), hereinafter referred to as "pamoate", 2-naphthalene-sulfonate, hereinafter referred to as "napsylate", methanesulfonate, hereinafter referred to as "mesylate", p-toluenesulfonate, hereinafter referred to as "tosylate", and the like.

It is another object of the present invention to provide a process for the preparation of compounds of formula II above, said process comprising treating 3-amino-N-[2-(5-dimethylaminomethylfuran-2-ylmethylthio)ethyl]benzamide of formula

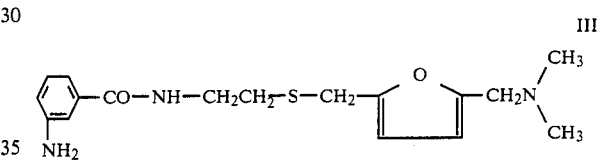

with a compound of formula $$Y=C=Z \qquad IV$$

wherein Y represents two methylthio groups and Z represents a N—CN or CH—$NO_2$ group or Y represents an oxygen or sulfur atom and Z represents a N—R group, where R has the above stated meaning in an organic solvent at a temperature between 20° C. and the boiling temperature of the solvent employed and, when Y represents two methylthio groups and Z represents a N—CN or CH—$NO_2$ group, the resulting product is treated with an amine of formula R—$NH_2$ wherein R is as hereinabove defined, in an organic solvent; and the product thus obtained is optionally converted into its pharmaceutically acceptable salts.

An alcohol such as methanol, ethanol or isopropanol is an advantageous reaction solvent, ethanol being particularly preferred.

It is a further object of the present invention to provide the novel intermediate 3-amino-N-[2-(5-dimethylaminomethylfuran-2-ylmethylthio)ehtyl]benzamide of formula III above, as well as its addition salts.

Said compound, which is not described in literature and which is not included in the French published patent application No. 2 471 376, represents the key-intermediate for the process of the present invention but it is also useful for the preparation of the amindobenzamides described in the European published patent application No. 69 664.

In fact, it has been found that starting from the novel amine III the whole series of amidobenzamides described in the above-mentioned European patent specification may be prepared by simple reaction with a functional derivative of a carboxylic or sulfonic acid. Thus, the preparation of appropriate intermediates for each synthesis may be avoided.

The 3-amino-N-[2-(5-dimethylaminomethylfuran-2-ylmethylthio)ethyl]benzamide may be prepared by reduction of the corresponding nitro compound of formula

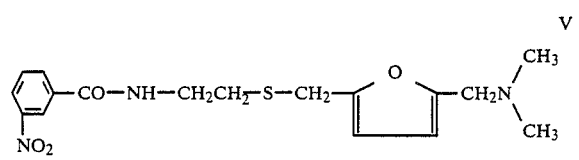

by using, as a reducing agent, the hydrogen nascent from the reaction of a metal, such as iron, and hydrochloric acid.

The product is isolated according to conventional methods as an oil fairly unstable at the heat and even at the room temperature that should be kept in the cold. In the form of a salt, it may be stored without problems; the oxalate is particularly preferred.

Anyhow, the 3-amino-N-[2-(5-dimethylaminomethylfuran-2-ylmethylthio)ethyl]benzamide free base obtained at the end of the reaction is pure enough for being converted into the benzamides of the present invention.

The starting compound V, namely 3-nitro-N-[2-(5-dimethylaminomethylfuran-2-ylmethylthio)ethyl]benzamide, is a new product too which may be easily prepared according to the process described in the above-mentioned French patent application published under the No. 2 471 376.

The benzamides of formula II above, as well as their pharmaceutically acceptable salts, act as selective antagonists of the histamine $H_2$ receptors and are therefore useful for the treatment of the ulcer disease.

The selective activity of the products of the present invention towards the receptors of type $H_2$ is confirmed by the absence of activity of type $H_1$ in the test of the contraction induced by histamine on the isolated guinea pig ileum.

The antagonistic activity of the compounds of the present invention towards the gastric histamine $H_2$ receptors has been confirmed in the test of the antisecretory activity based on the antagonism for the hypersecretion induced by histamine in the atropinized rat, according to the method of Ghosh and Schild (Br. J. Pharmacol. Chemother. 1858, 13, 54), modified according to Black et al. (Nature 1972, 236, 385). According to this test, a gastric acid hypersecretion is induced by intravenous infusion of a sub-maximal dose of histamine equivalent to 15 mcmol/kg/hour and the gastric secretion is measured by perfusion of a physiological solution at a constant speed in the stomach of the animal.

Table I shows, for 4 representative compounds of the present invention, indicated by their code numbers SR 57914, SR 57934, SR 57970 and SR 58028 A and for three reference compounds, the 2-cyano-1-methyl-3-[2-[[(5-methylimidazol-4-yl)methyl]thio]ethyl]guanidine, hereinafter designated by its International Non-proprietary Name "cimetidine", the N-[2-[[5-(dimethylamino)-methyl]furfuryl]thio]ethyl]-N'-methyl-2-nitro-1,1-ethenediamine, hereinafter designated by its International Non-proprietary Name "ranitidine" and the N-[2-(5-dimethylaminomethylfuran-2-ylmethylthio)ethyl]4-sulfamoylbenzamide, described in the above-mentioned published French patent application 2 471 376 and hereinafter designated "Compound A", the dose (in mcmol/kg by intravenous route in a single dose) which inhibits by 50% the gastric hypersecretion induced by histamine (ID50) as well as the relative potency of each product as compared to cimetidine. The ID50 represents the index of the gastric $H_2$-blocking action.

TABLE I

| Compound | ID50 (mcmol/kg) | Relative potency (cimetidine = 1) |
|---|---|---|
| Cimetidine | 0.95 | 1.00 |
| Ranitidine | 0.25 | 3.80 |
| Compound A | 2.26 | 0.42 |
| SR 57914 | 0.45 | 2.11 |
| SR 57934 | 1.53 | 0.62 |
| SR 57970 | 0.50 | 1.90 |
| SR 58028 A | 0.23 | 4.13 |

It results from this table that all the representative compounds of the present invention are more active than Compound A; their activity is comparable with or superior to that of cimetidine and one of them is at least as active as ranitidine.

The antisecretory activity of the products of the present invention has been evaluated in the cat bearing a gastric fistula according to the method of Emas et al. (Gastroenterology, 1960, 39, 771) by using, as hypersecretory agent, dimaprit at the dose of 640 mcg/kg/k. Under such conditions, a representative compound of the present invention, SR 57914, administered by intragastric route an hour before the perfusion of dimaprit, antagonizes in dose depending way the hypersecretion induced by dimaprit. Its activity is at least equal to that of cimetidine, utilized as reference compound.

The compounds of the present invention are only slightly toxic and are useful as drugs.

Thus, it is another object of the present invention to provide pharmaceutical compositions containing, as active ingredients, the compounds of formula II above, as well as their pharmaceutically acceptable addition salts.

In the pharmaceutical compositions of the present invention, for oral, sublingual, sub-cutaneous, intramuscular, intravenous, transdermic or rectal administration, the active ingredients of formula II above may be administered in unit forms of administration, in admixture with conventional pharmaceutical carriers, to animals and human beings for the treatment of gastric hypersecretion and ulcer disease. Appropriate unit forms of administration include the forms for oral administration, such as tablets, capsules, powders, granules and oral solutions or suspensions and the forms for sublingual and buccal administration, the forms for parenteral administration useful for a subcutaneous, intramuscular or intravenous injection, as well as the forms for rectal administration.

In order to obtain the desired antisecretory effect, the dose of active ingredient may vary between 0.1 and 100 mg per kg of body weight and per day.

Each unit dose may contain from 10 to 1000 mg, preferably from 50 to 500 mg, of active ingredient, in admixture with a pharmaceutical carrier. This unit dose may be administered from 1 to 4 times daily to treat the gastric hypersecretion and the ulcer disease.

The following examples illustrate the invention without, however, limiting it.

EXAMPLE 1

(a) 3-nitro-N-[2-(5-dimethylaminomethylfuran-2-ylmethylthio)ethyl]benzamide.

To a solution of 10.7 g of 2-(5-dimethylaminomethylfuran-2-ylmethylthio)ethylamine and 5.86 g of 4-dimethylaminopyridine in 100 ml of methylene chloride a solution of 9.5 g of 3-nitrobenzoyl chloride in 50 ml of methylene chloride is added dropwise, under stirring, at a temperature of from −5° to 0° C. The reaction mixture is stirred first 30 minutes at 0° C., then two hours at room temperature, afterwards it is evaporated to dryness under reduced pressure. The residue is taken up with 100 ml of N hydrochloric acid, the acid solution is washed twice with 30 ml of ethyl acetate and the pH is adjusted to 7.8. The mixture is extracted with ethyl acetate containing 10% of ethanol, the organic solution is dried on anhydrous sodium sulfate and evaporated. Thus the free base (16 g) is obtained as a pale yellow oil.

The oil thus obtained is dissolved in isopropanol and the resulting solution is treated with oxalic acid in isopropanol. Thus, 17.8 g of 3-nitro-N-[2-(5-dimethylaminomethylfuran-2-ylmethylthio)ethyl]benzamide oxalate are obtained; m.p. 146°–148° C.

(b) 3-amino-N-[2-(5-dimethylaminomethylfuran-2-ylmethylthio)ethyl]benzamide.

To a suspension of 13 g of 3-nitro-N-[2-(5-dimethylaminomethylfuran-2-ylmethylthio)ethyl]benzamide and 8 g of metallic iron, previously washed with 2N hydrochloric acid, in a mixture of 50 ml of water and 50 ml of methanol, concentrated hydrochloric acid is added dropwise and under stirring until pH 5, then the mixture is heated two hours with reflux. After cooling, the precipitate is filtered and thoroughly washed with methanol. The solution so obtained is evaporated under reduced pressure to eliminate the methanol. The pH of the aqueous solution is adjusted to 10 with sodium hydroxide and the inorganic precipitate which forms is eliminated after washing with ethanol. The solution is extracted 4 times with 40 ml of ethyl acetate containing 10% of ethanol, the solution is dried on anhydrous sodium sulfate and evaporated to dryness. Thus, 9 g of 3-amino-N-[2-(5-dimethylaminomethylfuran-2-ylmethylthio)ethyl]benzamide are obtained as an oil.

The product thus obtained is dissolved in ethanol and the alcoholic solution is treated with oxalic acid in 95% ethanol. Thus, 13 g of 3-amino-N-[2-(5-dimethylaminomethylfuran-2-ylmethylthio)ethyl]benzamide oxalate are obtained; m.p. 112°–115° C.

EXAMPLE 2

A solution of 2.3 g of methyl isocyanate in 10 ml of absolute ethanol is added dropwise to a solution of 6 g of 3-amino-N-[2-(5-dimethylaminomethylfuran-2-ylmethylthio)ethyl]benazmide in 50 ml of absolute ethanol. Then the mixture is left to stand 30 minutes at room temperature and afterwards it is heated at 50° C. for 2 hours. The solvent is evaporated under reduced pressure, the residue is taken up with diluted hydrochloric acid, the aqueous solution is extracted twice with 100 ml of ethyl acetate and treated with concentrated sodium hydroxide to clearly basic pH. The mixture is extracted three times with 100 ml of ethyl acetate, the organic phase is washed with water, dried on anhydrous sodium sulfate and evaporated to dryness. Thus, the 3-(3-methylureido)-N-[2-(5-dimethylaminomethylfuran-2-ylmethylthio)ethyl]benzamide is obtained as an oil which is dissolved in isopropanol and treated with a solution of 1.5 g of oxalic acid in isopropanol. A white solid is obtained which, after crystallization from 95% ethanol gives 4.5 g of 3-(3-methylureido)-N-[2-(5-dimethylaminomethylfuran-2-ylmethylthio)ethyl]benzamide oxalate; m.p. 156°–158° C. Code number: SR 57934A.

In the same manner, by reaction of 10 g of 3-amino-N-[2-(5-dimethylaminomethylfuran-2-ylmethylthio)ethyl]benzamide in 50 ml of ethanol with 9 g of phenyl isocyanate and crystallization from ethyl acetate, 7.5 g of 3-(3-phenylureido)-N-[2-(5-dimethylaminomethylfuran-2-ylmethylthio)ethyl]benzamide are obtained; m.p. 133°–135° C. Code number: SP 57972.

Similarly, starting from 5 g of 3-amino-N-[2-(5-dimethylaminomethylfuran-2-ylmethylthio)ethyl]benzamide and 1.4 g of methyl isothiocyanate in 60 ml of ethanol there is obtained crude 3-(3-methylthioureido)-N-[2-(5-dimethylaminomethylfuran-2-ylmethylthio)ethyl]benzamide which is crystallized from 95% ethanol to give 2.5 g of pure product; m.p. 155°–157° C.: Code number: SR 57914.

EXAMPLE 3

A mixture of 20 g of 3-amino-N-[2-(5-dimethylaminomethylfuran-2-ylmethylthio)ethyl]benzamide and 8.8 g of dimethyl cyanodithioiminocarbonate in 150 ml of absolute ethanol is heated with reflux for 30 hours, then it is concentrated under reduced pressure and the crude oil thus obtained is poured on a silica column and eluted with a mixture chloroform:methanol 4:1. The fairly pure fractions are collected and the solvent is evaporated under reduced pressure. Thus, 6.5 g of 3-(3-cyano-2-methylisothioureido)-N-[2-(5-dimethylaminomethylfuran-2-ylmethylthio)ethyl]benzamide are obtained as an oil which is mixed with 10 ml of a 33% solution of methylamine in ethanol. The mixture thus obtained is left to stand 48 hours at room temperature, then the excess of methylamine is eliminated under reduced pressure. Thus 5 g of an oil are obtained which is submitted to a flash chromatography on silica by eluting with a mixture chloroform:ethanol 1:1. The pure fractions are collected and evaporated, the residue is crystallized twice from isopropanol. Thus, 2.5 g of 3-(2-cyano-3-methylguanidino)-N-[2-(5-dimethylaminomethylfuran-2-ylmethylthio)ethyl]benzamide are obtained; m.p. 140°–142° C.

According to the above procedure, by reacting 0.02 mol of 3-amino-N-[2-(5-dimethylaminomethylfuran-2-ylmethylthio)ethyl]benzamide and 0.02 mol of 1,1-bis-methylthio-2-nitroethene in 50 ml of ethanol, the 3-[N-(1-methylthio-2-nitroethenyl)amino]-N-[2-(5-dimethylaminomethylfuran-2-ylmethylthio)ethyl]benzamide is obtained in 65% yield, said compound being then dissolved in ethanol and treated with a 33% solution of methylamine in ethanol to give the 3-[N-(1-methylamino-2-nitroethenyl)amino]-N-[2-(5-dimethylaminomethylfuran-2-ylmethylthio)ethyl]benzamide as a practically pure oil. The product thus obtained is transformed into its oxalate in 95% ethanol. After crystallization from 200 ml of ethanol, the pure oxalate is obtained in 43% yield; m.p. 175°–177° C.

EXAMPLE 4

Tablets comprising one of the products described in Examples 2 and 3, having the following composition:

| | |
|---|---|
| active substance | 150 mg |
| microcrystalline cellulose | 75 mg |

| -continued | |
|---|---|
| talc | 15 mg |
| polyvinylpyrrolidine | 30 mg |
| precipitated silica | 25 mg |
| magnesium stearate | 5 mg |

All the ingredients, except the lubricant, are intimately mixed in a mixing machine for 15 minutes, then the mixture is bound by gradual addition of water. The mass is passed through a 1.25 mm sieve. The granules are dried in a fluidized bed dryer until a relatively small degree of residual moisture is obtained (about 2% water). To the uniform mass there is added the lubricant and tablets are prepared by compression. Weight of a tablet: 300 mg.

In the same manner, tablets comprising 250 mg of active substance are prepared.

EXAMPLE 5

Capsules comprising one of the products described in Examples 2 and 3, having the following composition:

| active substance | 200 mg |
|---|---|
| cornstarch | 90 mg |
| talc | 10 mg |

The active substance and the excipients are intimately mixed and the mixture thus obtained is introduced into capsules of gelatine of dimension 1. Contents of a capsule: 300 mg.

We claim:

1. The 3-amino-N-[2-(5-dimethylaminomethylfuran-2-yl-methylthio)ethyl]benzamide of formula

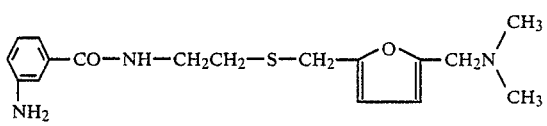

or an acid addition salt thereof.

* * * * *